(12) United States Patent
Riddoch et al.

(10) Patent No.: US 11,351,276 B2
(45) Date of Patent: Jun. 7, 2022

(54) RADIOPHARMACEUTICAL COMPOSITIONS OF RADIOACTIVE HALOGENATED BENZYLGUANIDINE

(71) Applicant: Jubilant Draximage Inc., Kirkland (CA)

(72) Inventors: Robert William Riddoch, Pierrefonds (CA); Abmel Xiques Castillo, Saint Laurent (CA)

(73) Assignee: Jubilant Draximage Inc., Kirkland (CA)

( * ) Notice: Subject to any disclaimer, the term of this patent is extended or adjusted under 35 U.S.C. 154(b) by 0 days.

(21) Appl. No.: 16/447,155

(22) Filed: Jun. 20, 2019

(65) Prior Publication Data

US 2019/0388567 A1    Dec. 26, 2019

Related U.S. Application Data

(60) Provisional application No. 62/688,470, filed on Jun. 22, 2018.

(51) Int. Cl.
| | |
|---|---|
| *A61K 51/00* | (2006.01) |
| *A61M 36/14* | (2006.01) |
| *A61K 51/04* | (2006.01) |
| *A61K 47/22* | (2006.01) |
| *A61K 47/12* | (2006.01) |
| *C07B 59/00* | (2006.01) |
| *A61K 9/19* | (2006.01) |
| *A61K 47/10* | (2017.01) |
| *A61K 9/107* | (2006.01) |

(52) U.S. Cl.
CPC .............. *A61K 51/04* (2013.01); *A61K 9/107* (2013.01); *A61K 9/19* (2013.01); *A61K 47/10* (2013.01); *A61K 47/12* (2013.01); *A61K 47/22* (2013.01); *C07B 59/001* (2013.01)

(58) Field of Classification Search
CPC ........ A61K 51/04; A61K 47/22; A61K 47/12; A61K 9/19; A61K 47/10; A61K 9/107; C07B 59/001

USPC ......................................................... 424/1.85
See application file for complete search history.

(56) References Cited

U.S. PATENT DOCUMENTS

| 4,880,615 A * | 11/1989 | Charleson | A61K 51/12 |
| | | | 424/1.37 |
| 2009/0005595 A1 * | 1/2009 | Janssen | A61K 47/12 |
| | | | 564/237 |

FOREIGN PATENT DOCUMENTS

WO    WO-2011147762 A2 *    12/2011    .......... A61K 51/121

OTHER PUBLICATIONS

Sharp et al. RadioGraphics 2016, 36, 258-278. (Year: 2016).*
Ohshima et al., "Antitumor effects of radionuclide treatment using a-emitting meta-211 At-astato-benzylguanidine in a PC12 pheochromocytoma model", Eur. J. Nucl. Med. Mol. Imaging, 2018, 45(6), 999-1010.
Pandit-Taskar et al., Labelling cold MIBG with fluor-18 leads to 18F-Meta Fluorobenzyl Guanidine (18F-MFBG). J. Nucl. Med., Jun. 2017, Published online Jul. 13, 2017; 59: 147-153.

* cited by examiner

*Primary Examiner* — Michael G. Hartley
*Assistant Examiner* — Sean R Donohue
(74) *Attorney, Agent, or Firm* — BakerHostetler

(57) ABSTRACT

The present disclosure concerns radiopharmaceutical compositions of radioactive halogenated benzylguanidine (such as radioiodinated MIBG) or a pharmaceutically acceptable salt, hydrate, or solvate thereof. In a preferred embodiment, the composition has at least 97% of radiochemical purity for at least 4 days. Advantageously, the compositions of the present disclosure may be devoid of parabens, which are carcinogenic and yet are used in known radioactive MIBG compositions. The present disclosure also provides processes of preparing a radioactive halogenated benzylguanidine composition. The compositions of the present disclosure can be used in diagnosis and treatment of various diseases.

16 Claims, No Drawings

RADIOPHARMACEUTICAL COMPOSITIONS OF RADIOACTIVE HALOGENATED BENZYLGUANIDINE

CROSS-REFERENCE TO RELATED APPLICATIONS

The present application claims priority to U.S. Provisional Application No. 62/688,470, filed on Jun. 22, 2018, the entire contents of which are herein incorporated by reference.

FIELD

The present disclosure is concerned with radiopharmaceutical compositions of radioactive halogenated benzylguanidine (such as radioactive iodine MIBG), or a pharmaceutically acceptable salt, hydrate or solvate thereof. In a preferred embodiment, the compositions have at least 97% of radiochemical purity for at least 4 days. Advantageously, the compositions of the present disclosure may be devoid of parabens, which are found to be carcinogenic and yet are used in known compositions for stabilizing MIBG compositions. The present disclosure also provides processes of preparing a radioactive halogenated benzylguanidine composition. The compositions of the present disclosure can be used in diagnosis and treatment of various diseases.

BACKGROUND

Radioactive iodine MIBG is a radiopharmaceutical used in a scintigraphy method called MIBG scan. The radioisotope of iodine that is commonly used for labeling is $^{123}$I or $^{131}$I. $^{131}$I-MIBG also called Iobenguane Sulfate I-131 Injection, is used as an adjunctive diagnostic agent in the localization of primary or metastatic pheochromocytomas and neuroblastomas. MIBG has a structural formula as represented in Formula I.

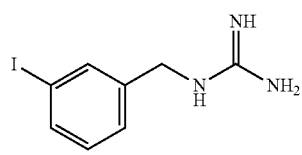

Formula I

Radioactive iodine MIBG is used in radiopharmaceutical compositions. It was marketed by Pharmalucence Inc. as a solution for intravenous injection (formulation discontinued as per USFDA). This radioactive iodine MIBG composition contains iobenguane sulfate, 85.1 MBq (2.30 mCi) of $^{131}$I (as iobenguane sulfate $^{131}$I at calibration), sodium acetate, acetic acid, sodium chloride, methyl paraben, propyl paraben and benzyl alcohol. This composition contains parabens such as methyl and propyl paraben and it is known that use of parabens is not safe and can lead to certain tumors like breast tumors (Rita Arditti (Jun. 9, 2004). "Cosmetics, parabens, and breast cancer". Organic Consumers Association).

U.S. Pat. No. 4,880,615 discloses use of radioprotectants like nicotinamide, nicotinic acid and ascorbic acid in order to stabilize radioactive MIBG compositions. However, examples shown in this patent were unable to achieve radiochemical purity of more than 96% for four days. Since stability, high radiochemical purity during the shelf life is critical for commercialization of any radiopharmaceutical product, there exists a need to improve the stability and radiochemical purity of $^{123}$I or $^{131}$I MIBG compositions using iodinated MIBG having high activity.

Other radioisotopes are used for labelling cold MIBG, such as $^{211}$At, $^{18}$F and $^{76}$Br. Labelling cold MIBG with astatine-211 provides meta-$^{211}$At-astato-benzylguanidine ($^{211}$At-MABG), and this radio-analog discussed by Ohshima et al. Eur. J. Nucl. Med. Mol. Imaging. 2018, 45(6) pp. 999-1010. Labelling cold MIBG with fluor-18 leads to $^{18}$F-Meta Fluorobenzyl Guanidine ($^{18}$F-MFBG), which was reported by Pandit-Taska et al. J. of Nucl. Med., Published online Jul. 13, 2017 (Doi: 10.2967/jnumed.117.193169). Labelling cold MIBG with bromo-76 results in m-bromo-benzylguanidine ($^{76}$Br-MBBG) and its use as an alternative to $^{131}$I-MIBG was discussed in Jerome Clerc thesis in 1997 (http://www.theses.fr/1997PA112206).

SUMMARY

The present disclosure provides radiopharmaceutical compositions of radioactive halogenated benzylguanidine that has a high radioactive purity.

The present inventors have surprisingly found that stable compositions of radioactive MIBG or its pharmaceutically acceptable salts, hydrates and solvates thereof can be made without use of parabens in the composition. It has been surprisingly found that maintaining a ratio of radioprotectants like benzyl alcohol and niacinamide in the composition leads to a stable composition with radiochemical purity of at least 97% for at least four days. The combination of benzyl alcohol and niacinamide provides synergistic effect in stabilizing radiopharmaceutical compositions of the present disclosure.

The present disclosure also provides radiopharmaceutical compositions of radioactive halogenated benzylguanidine having a high radioactive purity that remain stable for a suitable period of time which covers the period from their preparation, transportation and administration to the patient. Preferably, this suitable period is of 2, 3, 4, or 5 days.

The present disclosure further provides radiopharmaceutical compositions of radioactive halogenated benzylguanidine that are exempt of paraben.

The present disclosure concerns any of the following Aspects:

Aspect 1. A radiopharmaceutical composition comprising a radiohalogenated benzylguanidine or a pharmaceutically acceptable salt, hydrate or solvate thereof, wherein the composition has a radiochemical purity of at least 95% at two days following its preparation from its constituent ingredients.

Aspect 2. The radiopharmaceutical composition of aspect 1, wherein the radiochemical purity is at least 95% at four days following its preparation.

Aspect 3. The radiopharmaceutical composition of aspect 1 or aspect 2, wherein the radiochemical purity is at least 97% at two days following its preparation.

Aspect 4. The radiopharmaceutical composition of any preceding aspect, wherein the radiochemical purity is at least 97% at four days following its preparation.

Aspect 5. The radiopharmaceutical composition of any preceding aspect, wherein the composition has a radiochemical purity of at least 99% at the time immediately following its preparation.

Aspect 6. The radiopharmaceutical composition of any preceding aspect, the radiohalogenated benzylguanidine or a pharmaceutically acceptable salt, hydrate or solvate thereof, contains a radioactive halogen which is selected from the group consisting of $^{123}$I, $^{124}$I, $^{125}$I, $^{131}$I, $^{211}$At, $^{18}$F and $^{76}$Br.

Aspect 7. The radiopharmaceutical composition of aspect 6, wherein radioactive halogen which is selected from the group consisting of $^{123}$I, $^{124}$I, $^{125}$I and $^{131}$I.

Aspect 8. The radiopharmaceutical composition of aspect 7, wherein radioactive halogen is $^{131}$I.

Aspect 9. The radiopharmaceutical composition of any preceding aspect, wherein the composition does not include a paraben.

Aspect 10. The radiopharmaceutical composition of any preceding aspect, wherein the composition has a radiochemical purity of at least 95% at two days following its preparation when stored at any temperature from 78±3° C. to 25±3° C.

Aspect 11. The radiopharmaceutical composition of any preceding aspect, wherein the composition has a radiochemical purity of at least 95% at two days following its preparation when stored at a temperature of 5±3° C.

Aspect 12. The radiopharmaceutical composition of any preceding aspect, comprising benzyl alcohol and niacinamide.

Aspect 13. The radiopharmaceutical composition of aspect 12, wherein the benzyl alcohol and niacinamide are present in the composition in a ratio of from 1:0.5 to 1:35.

Aspect 14. The radiopharmaceutical composition of aspect 13, wherein the benzyl alcohol and niacinamide are present in the composition in a ratio of from 1:0.8 to 1:32.

Aspect 15. The radiopharmaceutical composition of aspect 14, wherein the benzyl alcohol and niacinamide are present in the composition in a ratio of about 1:1.

Aspect 16. The radiopharmaceutical composition of aspect 14, wherein the benzyl alcohol and niacinamide are present in the composition in a ratio of about 1:0.8.

Aspect 17. The radiopharmaceutical composition of aspect 12, wherein the benzyl alcohol is present in a concentration from 0.9% (v/v) to 2.0% (v/v).

Aspect 18. The radiopharmaceutical composition of aspect 12, wherein the composition has a pH from 3.0 to 7.0.

Aspect 19. The radiopharmaceutical composition of aspect 18, wherein the pH is 5.0±0.1.

Aspect 20. The radiopharmaceutical composition of aspect 18, further comprising a buffer comprising sodium acetate and sodium chloride.

Aspect 21. The radiopharmaceutical composition of aspect 12, wherein the composition is prepared by a method comprising the steps of:

(i) combining benzyl alcohol with water to form a combination;

(ii) adding niacinamide to the combination of step (i), and mixing;

(iii) adjusting the pH of the combination from 3.0 to 7.0; and (iv) adding radiohalogenated benzylguanidine to the pH-adjusted combination of step (iii);

and wherein the method does not include the addition of paraben.

Aspect 22. The radiopharmaceutical composition of aspect 21, wherein step (ii) of the method further comprises the addition of sodium acetate and sodium chloride.

Aspect 23. The radiopharmaceutical composition of any preceding aspect, wherein the composition is a lyophilized powder, solution, suspension or emulsion.

Aspect 24. The radiopharmaceutical composition of any preceding aspect, wherein the composition is provided in a container selected from the group consisting of a vial, an ampoule, a prefilled syringe, and a capsule.

Aspect 25. A method for the detection or localization in a subject of primary or metastatic pheochromocytoma, neuroblastoma, paraganglioma, neuroendocrine tumor of gastroenteropancreatic tract, medullary thyroid carcinoma, or a disease resulting from myocardial ischemia and cardiomyopathy, the method comprising administering to the subject the radiopharmaceutical composition according to any of aspects 1-24, and, performing scintigraphic imaging in order to detect or localize the primary or metastatic pheochromocytoma, neuroblastoma, paraganglioma, neuroendocrine tumor of gastroenteropancreatic tract, medullary thyroid carcinoma, or a disease resulting from myocardial ischemia and cardiomyopathy in the subject.

Aspect 26. A method for diagnosing or treating in a subject pheochromocytoma, neuroblastoma, paraganglioma, or neuroendocrine tumor of the gastroenteropancreatic tract, the method comprising administering to the subject the radiopharmaceutical composition according to any of aspects 1-24.

The scope of the presently disclosed subject matter will be better understood in light of the following detailed description thereof.

DETAILED DESCRIPTION

In one aspect, provided herein are radiopharmaceutical compositions of radiohalogenated benzylguanidine, a pharmaceutically acceptable salt thereof, a pharmaceutically acceptable hydrate thereof, or a pharmaceutically acceptable solvate thereof. It should be understood herein that the expression "a pharmaceutically acceptable salt thereof, a pharmaceutically acceptable hydrate thereof, or a pharmaceutically acceptable solvate thereof" has the exact same meaning herein than "a pharmaceutically acceptable salt, hydrate or solvate thereof" and the latter is used for sake of conciseness. Radioactive halogenated benzylguanidine includes radioactive iodine metaiodobenguanidine (radioactive iodine MIBG or radioiodinated MIBG) that contains an iodine radioisotope, which is preferably selected from the group consisting of $^{123}$I, $^{124}$I, $^{125}$I and $^{131}$I. Benzylguanidine and benguanidine are used interchangeably herein. Also, the terms "radiohalogenated" and "radioactive halogenated" are used interchangeably herein and are intended to mean the same. The expression "m-iodobenzylguanidine" can be used interchangeably with "metaiodobenzylguanidine", "metaiodobenguanidine", "MIBG", and "iobenguane".

In another aspect, the radiopharmaceutical compositions of the present disclosure comprise radioactive halogenated benzylguanidine or a pharmaceutically acceptable salt, hydrate or solvate thereof, wherein the radioactive halogenated benzylguanidine contains a radioactive halogen which is preferably selected from the group consisting of $^{123}$I, $^{124}$I, $^{125}$I, $^{131}$I, $^{211}$At, $^{18}$F and $^{76}$Br. The radioactive halogenated benzylguanidine is preferably radioactive m-iodobenzylguanidine. The radioisotope of iodine is preferably $^{123}$I radioisotope, $^{124}$I radioisotope, $^{125}$I radioisotope or $^{131}$I radioisotope, and more preferably $^{123}$I radioisotope or $^{131}$I radioisotope. In an embodiment, the composition of the present disclosure further comprises one or more additive agents. Said additive agents comprise niacinamide and benzyl alcohol, and may further comprise sodium acetate.

The term "m-iodobenzylguanidine" refers to a compound having formula $C_8H_{10}IN_3$ and having molar mass of 275.09 g/mol. Salt, hydrate and solvate of "radiohalogenated benzylguanidine" are also encompassed by the present disclosure. Preferably, the salt of radiohalogenated benzylguanidine is a non-nucleophilic salt, such as nitrate, sulfate or hemi-sulfate. According to the present disclosure, the preferred salt is a hemi-sulfate salt. In another preferred embodiment, the salt of radiohalogenated benzylguanidine is used in the composition. In another preferred embodiment, the hydrate of radiohalogenated benzylguanidine is used in the composition.

In another aspect, the radiopharmaceutical compositions according to the present disclosure comprise radiohalogenated benzylguanidine or a pharmaceutically acceptable salt, hydrate or solvate thereof, niacinamide and benzyl alcohol.

In another aspect, the radiopharmaceutical compositions according to the present disclosure comprise radiohalogenated benzylguanidine or a pharmaceutically acceptable salt, hydrate or solvate thereof, niacinamide, benzyl alcohol, and sodium acetate.

In another aspect, the radiopharmaceutical compositions of the present disclosure are devoid of paraben. Parabens includes without limitation methyl paraben, propyl paraben, butyl paraben, ethyl paraben and the like.

In another aspect, the radioactivity concentration of the radiopharmaceutical compositions of the present disclosure ranges from about 5 mCi/ml to 1 Ci/ml, from about 10 mCi/ml to 500 mCi/ml, from about 10 to 100 mCi/ml, from about 10 to 50 mCi/ml, or about 30 mCi/ml.

In another aspect, the radiochemical purity of the compositions according to the present disclosure is at least 99% upon its preparation. In an embodiment, the radiochemical purity of 99% is present on day 0 or day 1 upon the preparation of the composition. The term "radiochemical purity" as used herein, designates the percentage of radioisotopes that are attached or bound within benzylguanidine per the total of radioactivity in the composition. Radiochemical impurity herein is represented by the radioisotopes that are free (or unbound) in the composition. Day 0 indicates immediately after preparation of the composition; and day 1 means 24 hours after preparation of the same.

In yet another aspect, the radiochemical purity of the compositions according to the present disclosure is at least 97% for at least two days after the preparation of the composition. In yet another aspect, the radiochemical purity of the composition according to the present disclosure is at least 97% for at least four days after the preparation of the composition. In an embodiment of the invention, the composition is stored at 5±3° C. (or 2-8° C.). In another embodiment of the invention, the composition is stored at a temperature between 2° C. and 30° C. In a further aspect, the radiochemical purity of the composition according to the present disclosure is at least 95% for at least two days after the preparation of the composition. In another further aspect, the radiochemical purity of the composition according to the present disclosure is at least 95% for at least four days after the preparation of the composition. In an aspect of the present disclosure, the radiochemical purity of the composition is at least 99%, 98%, 97%, 96%, 95% or 94% for at least 0, 1, 2, 3, 4 or 5 days from the day of its preparation when stored on dry ice (−78±3° C.), freezer (−18±3° C.), refrigerator (at 5±3° C.), at room temperature (25±3° C.) or at any temperature in between −78±3° C. and 25±3° C. In a preferred embodiment, the composition is frozen on dry ice after its preparation. The composition is preferably shipped frozen on dry ice; the dry ice sublimes during the transportation. Therefore, once received at destination, the composition is at temperature that can vary from dry ice temperature to room temperature. Upon receipt, the composition is preferably removed from its shipping container and placed into a refrigerator at 5±3° C. Stability of composition is maintained up to its expiry date. In another embodiment of the invention, the composition is not frozen after its preparation and shipped at a refrigerated temperature of about refrigerator (at 5±3° C.). In an embodiment, the composition of the present disclosure expires at 23:59, two days after the date of its manufacture. In another embodiment, the composition of the present disclosure expires at 23:59, four days after the date of its manufacture.

In an embodiment, the resulting radiochemical purity of a composition immediately after its preparation is at least 99%, 98% or 97%. In another embodiment, the resulting radiochemical purity of the composition two days after its preparation is at least 98%, 97%, 96% or 95% when stored at a temperature from −78±3° C. to 25±3° C.

Radiochemical purity of a composition of radioactive halogenated benzylguanidine is the amount of radioactive halogen that is bound within the benzylguanidine compared to the total of radioactive halogen that is present in the composition. Radiochemical purity is measured by a variety of analytical techniques such as high performance liquid chromatography (HPLC), paper chromatography, thin-layer chromatography and electrophoresis. After separation, the distribution of radioactivity on the chromatogram is determined using an appropriate radiation detector. The radiochemical purity of a composition is the percentage of the stated radionuclide that is present in the stated molecule. The composition should maintain an acceptable radiochemical purity limit during the whole shelf-life. Radiochemical impurities may arise during the preparation of the material or during storage, chemical decomposition or, because of radiation decomposition (radiolysis).

The compositions of the present disclosure may further comprise one or more excipient or additives. The term "excipient or additive" means a component that has no diagnostic or therapeutic function. Examples of excipients are, without limitation, buffering components, acids, bases, osmolality adjusting agents, tonicity modifying agents, fillers, stabilizers, radioprotectants and lyoprotectants. The excipients that are useful in preparing a pharmaceutical composition are generally safe, non-toxic and are acceptable for human pharmaceutical use. Combination of excipients performing the same function may also be used to achieve desired composition characteristics.

When the radiopharmaceutical composition of the present disclosure is intended for parenteral administration, it may include one or more pharmaceutically acceptable carriers and excipients, including, but not limited to, aqueous vehicles, water-miscible vehicles, non-aqueous vehicles, stabilizers, solubility enhancers, isotonic agents like mannitol, glucose, trehalose, dextran, buffering agents, antioxidants, suspending and dispersing agents, wetting or emulsifying agents, complexing agents, sequestering or chelating agents, cryoprotectants, lyoprotectants, thickening agents, pH adjusting agents and inert gases, radioprotectants like benzyl alcohol, niacinamide, ascorbic acid, gentisic acid, sodium sulfite, sodium metabisulfite, para amino benzoic acid (PABA), pyridoxine, and pyridoxal. When the pharmaceutical composition of the present disclosure is intended for oral administration, it may be in a liquid form or a solid form.

In one embodiment, the compositions of the present disclosure comprise radioactivehalogenated benzylguanidine or a pharmaceutically acceptable salt, hydrate or solvate thereof, in combination with a tonicity adjuster, a buffer and a compound selected from the group consisting of a stabilizer, a preservative, or a radioprotectant.

According to the present disclosure, the "radioprotectant" is an ingredient which prevents the radiolysis of the composition and helps in stabilizing the radiopharmaceutical compositions. Radioprotectant can be selected from the consisting of antioxidants, buffering agents, stabilizers, preservatives or combinations thereof.

According to the invention, the "stabilizer" can be selected from the group consisting of aminoethyl sulfonic acid, niacinamide, L-arginine, butylhydroxyanisol, L-cysteine, cysteine hydrochloride, diethanolamine, diethylene triamine pentaacetic acid, human serum albumin, hydrolyzed gelatin, inositol, D,L-methionine, polyoxyethylene castor, potassium pyrosulfite, potassium thiocyanate, sodium gluconate, sodium thioglycolate, trienthanolamine, zinc chloride solution, ascorbic acid, gentisic acid, nicotinic acid, para amino benzoic acid (PABA), ethyl gallate, propyl gallate, riboflavin-5-phosphate, benzyl alcohol, and a combination thereof.

According to the present disclosure, the "preservative" can be selected from the group consisting of benzalkonium chloride, benzethonium chloride, benzyl alcohol, chlorobutanol, m-cresol, phenol, 2-penoxyethanol, phenyl mercuric nitrate, thimerosal or combinations thereof.

According to the present disclosure, the "buffer" or "buffering agent" can be selected from group consisting of sodium citrate, acid citrate, disodium citrate, trisodium citrate, sodium acetate, glacial acetic acid, sodium phosphate, monobasic potassium phosphate, dibasic potassium phosphate, monobasic sodium phosphate, dibasic sodium phosphate, tribasic sodium phosphate, tris base, tris acetate, Tris HCl, meglumine, tartarate sodium/acid, sodium carbonate, sodium dihydrogen phosphate, and combinations thereof.

The "inert gas" according to the present disclosure can be selected from group consisting of helium, neon, argon, nitrogen or combinations thereof. In an embodiment of the invention, an inert gas is used to replace the presence of air in a vial containing the composition of the present disclosure during transportation and storage, and until the vial is opened.

In one embodiment, the composition according to current invention is devoid of paraben. Paraben includes without limitation any alkyl paraben such as methyl paraben, propyl paraben, butyl paraben, ethyl paraben and the like.

In one embodiment, the radioactivity of the radiopharmaceutical composition ranges from about 1 mCi to about 1 Ci per container, about 25 mCi to about 700 mCi per container, or about 30 mCi to about 450 mCi per container. In one embodiment, the volume of the radiopharmaceutical composition ranges from about 0.4 ml to about 50 ml per container, from about 0.4 ml to about 10 ml per container, from about 0.4 ml to about 2 ml per container, or of about 1 ml per container. In one embodiment, the concentration of radiohalogenated benzylguanidine in the radiopharmaceutical composition is from about 0.10 mg/ml to about 10 mg/ml, from about 0.50 mg/ml to about 2 mg/ml, or of about 0.83 mg/ml.

In a preferred embodiment, the preparation of radiohalogenated benzylguanidine (labelling reaction) is obtained by the replacement of its non-radio-active iodine atom with a radioactive isotope of halogen such as a radioisotope of iodine, a radioactive isotope of fluor, a radioactive isotope of brome or a radioactive isotope of astitine. In an embodiment, the process consists of adding to a vial containing a given amount of cold MIBG (i.e. non-radioactive MIBG), the appropriate volume of copper catalyst solution, buffer solution and radioactive halogen isotope solution. After adding a few anti-bumping granules, the vial is sealed and heated for 40-50 minutes. Upon that time the labelling reaction is completed and the reaction mixture is transferred with hot water into a purification column containing anion exchange resin. Most or all the content in copper catalyst is removed by the anion exchange resin. The purified labelled benzylguanidine is collected in a vial containing a diluent solution. Depending of the reaction yield and recovery and the customer requested dose, the labelled benzyl guanidine can be further diluted with the diluent solution and dispensed. In an embodiment, the radiopharmaceutical composition may contain trace of copper catalyst, and preferably no more than 0.1 mg/ml, preferably no more than 0.03 mg/ml, or preferably no more than 0.02 mg/ml.

In one embodiment of the present disclosure, the composition can be directly administered to the patient or can be further diluted with a suitable biocompatible diluent prior administration.

The term "about" as used herein preferably refers to ±10% of the values mentioned herein.

In one embodiment, the composition according to the present disclosure has a shelf-life of at least 5, 4, 3, or 2 days, and more preferably at least 2 days, and more preferably of at least 4 days.

In another embodiment of the present disclosure, a combination of niacinamide and benzyl alcohol is used to preserve radiochemical purity of the composition with high activity during shelf life of the product. Preferably, niacinamide and benzyl alcohol are present in an optimum ratio that provides an improved radiochemical purity during shelf-life of the composition. It has been found that benzyl alcohol and niacinamide provide a synergistic effect in stabilizing the radiopharmaceutical composition of present disclosure. Furthermore, the composition pH is preferably maintained in an optimum range i.e. from about 3 to 8, from about 3 to 7, from about 4 to 7.5, from about 4 to 6, from about 6 to 7.5, from about 6 to 7, from about 5 to 6, from about 4.5 to 5, or 5.0±0.1, or 4.5±0.1.

Niacinamide concentration in the composition of the present disclosure, is preferably about 0.5 to 70.0 g/100 ml, preferably about 0.5 to 10.0 g/100 ml, preferably about 1.0 to 5.0 g/100 ml, preferably about 1.0 to 2.0 g/100 ml, preferably about 1.5 to 2.0 g/100 ml, and preferably about 1.6 g/100 ml.

Benzyl alcohol concentration in the composition of the present disclosure, is preferably 2.0% (v/v) or lower, preferably from 0.01% (v/v) to 2.0% (v/v), preferably from 0.05% (v/v) to 2.0% (v/v), preferably from 0.9% (v/v) to 2.0% (v/v), preferably from 0.05% (v/v) to 1.6% (v/v), preferably from 0.05% to 1.8%, preferably from 0.05% to 1.6%, preferably from 0.05% to 1.2%, preferably about 0.01%, preferably about 0.05%, preferably about 0.5%, preferably about 0.9%, preferably about 1.0%, or preferably about 1.6%. The concentration of benzyl alcohol should not exceed toxicity level for intravenous administration as set forth by Health Canada, FDA, EMA, and other regulatory agencies.

In another embodiment, the composition according to the present disclosure has a radiochemical purity of at least 90% and preferably at least 91%, 92%, 93%, 94%, 95%, 96%, 97%, 98%, or 99%.

In another embodiment of present disclosure, the radiopharmaceutical composition comprises radiohalogenated benzylguanidine or a pharmaceutically acceptable salt, hydrate or solvate thereof, and one or more stabilizers that is/are not selected from the group consisting of parabens. Said one or more stabilizers is preferably a combination benzyl alcohol and niacinamide. Optionally, the composition of the present disclosure also comprises a buffer. Preferably, said buffer comprises a combination of sodium acetate trihydrate and sodium chloride. Any pharmaceutically acceptable buffers are contemplated to prepare the composition of the present disclosure as long as the desired pH is reached and maintained. Preferably, the concentration of sodium acetate trihydrate varies between 0.01 and 20 mg/ml, between 0.05 and 10 mg/ml, between 0.05 and 5 mg/ml, between 0.1 and 2 mg/ml, between 0.5 and 2 mg/ml, or from 1.0 to 1.3 mg/ml.

In another aspect, the radiopharmaceutical composition of the present disclosure, comprises radiohalogenated benzylguanidine, benzyl alcohol and niacinamide, wherein the ratio of benzyl alcohol:niacinamide ranges from about 1:1 to about 1:35, preferably from about 1:1 to about 1:15, preferably from about 1:1 to about 1:10, preferably from about 1:1 to about 1:5, preferably from about 1:1 to about 1:2. In yet another aspect of the present disclosure, the ratio of niacinamide:benzyl alcohol ranges from about 1:1 to about 1:5, preferably from about 1:1 to about 1:3, and preferably from about 1:1 to about 1:2. Preferably, the ratio of benzyl alcohol:niacinamide is from about 1:0.5 to 1:35, preferably from about 1:0.8 to 1:32, preferably from about 1:0.8 to 1:10, preferably from about 1:0.8 to 1:2, preferably from about 1:0.8 to 1:2, preferably about 1:1, preferably about 1:0.9, or preferably about 1:0.8. In another embodiment, the composition comprises a ratio of niacinamide:benzyl alcohol that is from about 1:1 to 1:5, preferably 1:1 to 1:3.

In another aspect, the radiopharmaceutical composition of the present disclosure is suitable for oral or parental administration. Parental administration includes intravenous administration. In one embodiment of the present disclosure, the pharmaceutical composition provided herein may be formulated in any dosage form that is suitable for parenteral administration, including solution, lyophilized powder, suspension, emulsion, micelle, liposome, microsphere, nanosystem, and solid form suitable for dissolution or suspension in a liquid prior to administration. In one embodiment of the present disclosure, the pharmaceutical composition provided herein may be formulated in any dosage form that is suitable for oral administration.

In one embodiment, the present disclosure also provides a method of preparing a pharmaceutical composition of radiohalogenated benzylguanidine, or a pharmaceutically acceptable salt, hydrate or solvate thereof.

The method preferably comprises the steps of:
(i) mixing benzyl alcohol with water;
(ii) adding niacinamide and optionally sodium acetate and/or sodium chloride to the solution prepared at step (i);
(iii) mixing the solution of step (ii);
(iv) optionally adjusting the pH between 3.0-7.0;
(v) optionally adding water to the solution prepared at step (iv) for adjusting the total volume of the solution; and
(vi) mixing radiohalogenated benzylguanidine with the solution of step (v); and
(vii) optionally filter the solution of step (vi).

In another aspect of the present disclosure, provided herein is a method for preparing a radiopharmaceutical composition of radiohalogenated benzylguanidine comprising:
(i) preparing a solution of benzyl alcohol and water;
(ii) adding niacinamide, sodium acetate and sodium chloride to the solution of step (i);
(iii) mixing the solution of step (ii)
(iv) optionally adjusting the pH to about 5.0;
(iv) completing the solution of step (iv) with water until the desired volume is reached;
(v) adding radiohalogenated benzylguanidine to the solution of step (iv); and
(vi) optionally filtering the solution of step (v).

Water used herein is preferably water for injection. Adjusting the pH is performed with addition of an acid or a base, wherein said acid is preferably HCl or sodium chloride, and said base is preferably NaOH or sodium acetate. The filtration step (vii) is optional and can be performed as a sterilization step. Preferably, a 0.22 µm pore size filter is used. In an embodiment of the invention, the method is exempt of addition of paraben at any step thereof.

In an embodiment, the resulting radiochemical purity of the composition within 24 hours of its preparation (i.e. at day 0) is at least 99%, 98% or 97%. In another embodiment, the resulting radiochemical purity of the composition two days after its preparation is at least 98%, 97%, 96% or 95% when stored between −78±3° C. and 25±3° C.

The pharmaceutical composition provided herein may be formulated for single or multiple dosage administration. The single dosage formulation can be packaged in an ampoule, a vial, a syringe, or a prefilled syringe. The single dosage formulation can be packaged into one or more capsules. The final composition of present disclosure is preferably packed in a 30 mL Type I glass vial capped with Teflon-coated, butyl rubber stopper and aluminium seal. In one embodiment of the present disclosure, the composition can be filled into a container such as a vial, an ampoule, or a prefilled syringe of 0.5 ml, 1 ml, 2 ml, 5 ml, 10 ml, 20 ml, 25 ml, 30 ml, 60 ml or 100 ml.

In yet another aspect, the radiopharmaceutical composition of the present disclosure are suitable for use in the detection and localization of primary or metastatic pheochromocytoma, neuroblastoma, paraganglioma, neuroendocrine tumors of gastroenteropancreatic tract, medullary thyroid carcinoma, and diseases resulting from myocardial ischemia and cardiomyopathy. The composition of the present disclosure is useful for scintigraphic assessment of sympathetic innervation of the myocardium. The composition of the present disclosure is also useful for the treatment of patients with malignant or recurrent pheochromocytoma, neuroblastoma, paraganglioma (PPGL), or neuroendocrine tumors of the gastroenteropancreatic tract.

Having described the invention with reference to certain preferred embodiments, other embodiments will become apparent to one skilled in the art from consideration of the specification. The invention is further defined by reference to the following examples describing in details radiopharmaceutical compositions of the present disclosure. It will be apparent to those skilled in the art that many modifications, both to materials and methods, may be practiced without departing from the scope of the invention. Following examples are set out to illustrate the invention and do not limit the scope of the invention.

EXAMPLES

The following examples are intended to further illustrate certain preferred embodiments of the invention and are not limiting in nature.

Example 1: MIBG Labelling Reaction

Radioactive MIBG is prepared by replacement of the non-radioactive iodine atom of cold MIBG with $^{131}$I. More particularly, in a vial containing 20 mg of cold MIBG, were added 1.3 Ci of Na$^{131}$I solution, copper catalyst solution, and sodium acetate pH 4.5 buffer solution. After adding a few anti-bumping granules, the vial is sealed and heated for 40-50 minutes. Then, the reaction mixture is transferred with hot water (eluant) into the purification column containing anion exchange resin. The purified labelled MIBG is collected into a vial containing the diluent solution (2×). The purification column is used to eliminate copper catalyst from the labelled MIBG solution.

Example 2: Preparation of the Diluent Solution

The diluent solution is prepared in a 2× concentration and in a 1× concentration. The diluent solution 2× is used to receive the labelled MIBG from the purification column and its eluant. For instance, if 8 ml of eluant (hot water) is used for eluting the labelled MIBG from the column, then 8 ml are used in the collecting vial, and thus the resulting concentration is 1×.

Six (6) diluent solutions 1× have been prepared in order to test the impact on various ratios of benzyl alcohol:niacinamide on the radiochemical purity of the radioiodinated MIBG composition of the present disclosure. The contents of these 6 diluent solutions 1× are as follow in Table 1.

TABLE 1

Diluent solutions 1X with various ratios of benzyl alcohol:niacinamide

| No. | Benzyl Alcohol (% v/v) | Niacinamide (g/100 ml) | pH | Ratio |
|---|---|---|---|---|
| 1 | 0 | 0 | 5.0 | 0:0 |
| 2 | 0 | 1.6 | 5.0 | 0:1 |
| 3 | 0.05 | 1.6 | 5.0 | 1:32 |
| 4 | 0.9 | 1.6 | 5.0 | 1:1.8 |
| 5 | 1.9 | 1.6 | 5.0 | 1:0.84 |
| 6 | 0.9 | 0 | 5.0 | 1:0 |

The diluent solution was prepared by:
i) Adding a volume of benzyl alcohol to water for injection, and mixing;
ii) Adding niacinamide to the solution of step (i), and mixing;
iii) Adjusting the pH of the solution of step (ii) to 5.0; and
iv) Adding water for injection so as to reach the desired final volume.

Example 3: Preparation of the Labelled MIBG Composition

A resulting labelled MIBG composition is obtained by collecting the purified labelled MIBG from the purification column in the diluent solution 2×, and mixing. The volume of elution (containing the labelled MIBG) is identical to the volume of diluent solution 2× in the collecting vial, in order to obtain a resulting concentration of the stabilizers and excipients of 1×.

When preparing doses of radioiodinated MIBG for administration and dilution is needed, the solution in the collecting vial is diluted with the diluent solution 1×.

Example 4: RadioChemical Purity (RCP) Assays with HPLC

Radiochemical purity (RCP) can be tested with several methods as described in the specification. In the present example, HLPC method was used as follow: Inject up to 20 uL of the labelled MIBG solution (sample) into the chromatographic system at a flow rate of 1 mL/min. Record the chromatogram. Two main peaks should be observed: one with a retention time of about 8 min for labelled MIBG and one at about 2 min for free iodine. Express the areas under the peaks as percentage of the total radioactivity measured. The percentage value for the labelled MIBG peak corresponds to the radiochemical purity (RCP) of the preparation.

Characteristics of the chromatographic system that have been used in this example are the following Table 2.

TABLE 2

Chromatographic system characteristics

| | |
|---|---|
| HPLC Column: | Luna 10µ, C18, 250 × 4.6 mm |
| Mobile Phase Mode: | Water (600 ml):acetonititrile (200 ml):TFA (4 ml) Isocratic |
| Acquisition Time: | 10 min |
| Flow rate: | 1 mL/min |
| UV Wavelength: | 229 nm |
| Radioactive detector | NaI |
| Injection Volume: | 10-100 µL |

Example 5: Variation of Benzyl Alcohol:Niacinamide Ratio Assays

Experiments were performed to determine the role of benzyl alcohol and niacinamide in the preservation of the radiochemical purity of $^{131}$I MIBG. In this experiment, six (6) samples were prepared each containing 50 mCi $^{131}$I MIBG in a composition of 2.5 mL total volume, and using the diluent solutions as described in Table I. Each $^{131}$I MIBG composition was stored for a period of four (4) days at 5±3° C. and the radiochemical purity (RCP) was monitored daily. Radiochemical purity was measured using HPLC method. The results of the radiochemical purity monitoring are reported in Table 3.

TABLE 3

Daily RCP results with varying ratios of benzyl alcohol:niacinamide

| $^{131}$I MIBG Composition with Diluent Solution No. | Benzyl Alcohol:Niacinamide Ratio | RCP (%) | | | | |
|---|---|---|---|---|---|---|
| | | Day 0 | Day 1 | Day 2 | Day 3 | Day 4 |
| 1 | 0:0 | 99 | 65 | 42 | 24 | 27 |
| 2 | 0:1 | | 97 | 96 | 95 | 92 |
| 3 | 1:32 | | 99 | 98 | 98 | 97 |
| 4 | 1:1.8 | | 98 | 99 | 98 | 97 |

TABLE 3-continued

Daily RCP results with varying ratios of benzyl alcohol:niacinamide

| $^{131}$I MIBG Composition with Diluent Solution No. | Benzyl Alcohol:Niacinamide Ratio | Day 0 | Day 1 | Day 2 | Day 3 | Day 4 |
|---|---|---|---|---|---|---|
| 5 | 1:0.84 | | 97 | 98 | 98 | 97 |
| 6 | 1:0 | | 92 | 80 | 69 | 68 |

Results from Table 3 clearly shows that the absence of niacinamide and benzyl alcohol (No. 1) is detrimental to the preservation of the radiochemical purity of $^{131}$I in MIBG; since after 4 days, said purity drastically went down from 99% to 27%. Results from Table 3 also clearly shows that neither niacinamide nor benzyl alcohol alone (Nos. 2 and 6) is sufficient to preserve the radiochemical purity of the composition, since the radiochemical purity has decreased to 92% and 68% respectively, after 4 four days. However, a significant preservation of the radiochemical purity of the $^{131}$I MIBG composition is obtained when benzyl alcohol and niacinamide are combined together (Nos. 3, 4 and 5). Although diluent solution Nos. 3, 4 and 5 have provided similar RCP, the diluent solutions No. 3 and No. 4 are advantageous in that they use a low concentration of benzyl alcohol. The resulting RCP results have shown that it is possible to maintain a radiochemical purity as high as 97% after 4 days when stored in the refrigerator, without using harmful excipients such as parabens.

While this invention has been described in detail with reference to certain preferred embodiments, it should be appreciated that the present disclosure is not limited to those precise embodiments. Rather, in view of the present disclosure, which describes the current best mode for practicing the invention, many modifications and variations would present themselves to those skilled in the art without departing from the scope, and spirit of this invention.

What is claimed:

1. A radiopharmaceutical composition comprising $^{131}$I-benzylguanidine or a pharmaceutically acceptable salt, hydrate or solvate thereof; and,
   radioprotectants comprising benzyl alcohol and niacinamide,
   wherein the benzyl alcohol and niacinamide are present in a ratio of about 1:0.8 to 1:32 wherein the composition has a pH of 5±0.1,
   wherein the radioactivity concentration of the composition is about 20 mCi/mL to about 1 Ci/mL,
   wherein the composition has a radiochemical purity of at least 99% at the time immediately following its preparation from its constituent ingredients, and,
   wherein the composition has a radiochemical purity of at least 97% following four days of storage at 5±3° C. after its preparation from its constituent ingredients.

2. The radiopharmaceutical composition of claim 1, wherein the composition does not include a paraben.

3. The radiopharmaceutical composition of claim 1, wherein the benzyl alcohol and niacinamide are present in the composition in a ratio of from 1:1 to 1:5.

4. The radiopharmaceutical composition of claim 3, wherein the benzyl alcohol and niacinamide are present in the composition in a ratio of from 1:1 to 1:3.

5. The radiopharmaceutical composition of claim 4, wherein the benzyl alcohol and niacinamide are present in the composition in a ratio of about 1:1.

6. The radiopharmaceutical composition of claim 1, wherein the benzyl alcohol and niacinamide are present in the composition in a ratio of about 1:1.8.

7. The radiopharmaceutical composition of claim 1, wherein the benzyl alcohol is present in a concentration from 0.9% (v/v) to 2.0% (v/v).

8. The radiopharmaceutical composition of claim 1, further comprising a buffer comprising sodium acetate and sodium chloride.

9. The radiopharmaceutical composition of claim 1, wherein the composition is prepared by a method comprising the steps of:
   (i) combining benzyl alcohol with water to form a combination;
   (ii) adding niacinamide to the combination of step (i), and mixing;
   (iii) adjusting the pH of the combination to 5±0.1; and
   (iv) adding $^{131}$I-benzylguanidine to the pH-adjusted combination of step (iii);
   and wherein the method does not include the addition of paraben.

10. The radiopharmaceutical composition of claim 9, wherein step (ii) of the method further comprises the addition of sodium acetate and sodium chloride.

11. The radiopharmaceutical composition of claim 1, wherein the composition is a lyophilized powder, solution, suspension or emulsion.

12. The radiopharmaceutical composition of claim 1, wherein the composition is provided in a container selected from the group consisting of a vial, an ampoule, a prefilled syringe, and a capsule.

13. A method for the detection or localization in a subject of primary or metastatic pheochromocytoma, neuroblastoma, paraganglioma, neuroendocrine tumor of gastroenteropancreatic tract, medullary thyroid carcinoma, or a disease resulting from myocardial ischemia and cardiomyopathy, the method comprising
   administering to the subject the radiopharmaceutical composition according to claim 1, and,
   performing scintigraphic imaging in order to detect or localize the primary or metastatic pheochromocytoma, neuroblastoma, paraganglioma, neuroendocrine tumor of gastroenteropancreatic tract, medullary thyroid carcinoma, or a disease resulting from myocardial ischemia and cardiomyopathy in the subject.

14. A method for diagnosing or treating in a subject pheochromocytoma, neuroblastoma, paraganglioma, neuroendocrine tumor of the gastroenteropancreatic tract, medullary thyroid carcinoma, or a disease resulting from myocardial ischemia and cardiomyopathy the method comprising administering to the subject the radiopharmaceutical composition according to claim 1; and, when diagnosis is required, performing scintigraphic imaging in order to diagnose the primary or metastatic pheochromocytoma, neuroblastoma, paraganglioma, neuroendocrine tumor of gastroenteropancreatic tract, medullary thyroid carcinoma, or a disease resulting from myocardial ischemia and cardiomyopathy in the subject.

15. The radiopharmaceutical composition according to claim 1, wherein the radioprotectants consist of benzyl alcohol and niacinamide.

16. The radiopharmaceutical composition according to claim 1, wherein the radioprotectants do not include gentisic acid.

* * * * *